US009549976B1

(12) United States Patent
Peabody et al.

(10) Patent No.: US 9,549,976 B1
(45) Date of Patent: Jan. 24, 2017

(54) AFFINITY SELECTION OF NIPAH AND HENDRA VIRUS-RELATED VACCINE CANDIDATES FROM A COMPLEX RANDOM PEPTIDE LIBRARY DISPLAYED ON BACTERIOPHAGE VIRUS-LIKE PARTICLES

(71) Applicants: David S. Peabody, Albuquerque, NM (US); Bryce Chackerian, Albuquerque, NM (US); Carlee Ashley, Albuquerque, NM (US); Eric Carnes, Albuquerque, NM (US); Oscar Negrete, Livermore, CA (US)

(72) Inventors: David S. Peabody, Albuquerque, NM (US); Bryce Chackerian, Albuquerque, NM (US); Carlee Ashley, Albuquerque, NM (US); Eric Carnes, Albuquerque, NM (US); Oscar Negrete, Livermore, CA (US)

(73) Assignees: STC.UNM, Albuquerque, NM (US); SANDIA CORPORATION, Albuquerque, NM (US)

( * ) Notice: Subject to any disclaimer, the term of this patent is extended or adjusted under 35 U.S.C. 154(b) by 0 days.

(21) Appl. No.: 14/081,629

(22) Filed: Nov. 15, 2013

Related U.S. Application Data

(60) Provisional application No. 61/727,389, filed on Nov. 16, 2012.

(51) Int. Cl.
*A61K 39/00* (2006.01)
*A61K 39/155* (2006.01)
(Continued)

(52) U.S. Cl.
CPC ....... *A61K 39/155* (2013.01); *G01N 33/56983* (2013.01)

(58) Field of Classification Search
None
See application file for complete search history.

(56) References Cited

U.S. PATENT DOCUMENTS 7,803,612 B2 * 9/2010 Audonnet ............ A61K 39/155
435/320.1
2009/0054246 A1 2/2009 Peabody et al.
(Continued)

FOREIGN PATENT DOCUMENTS

WO WO 2009105152 A2 * 8/2009
WO 2011082381 A2 7/2011
(Continued)

OTHER PUBLICATIONS

Harcourt et al., "Genetic Characterization of Nipah Virus, Bangladesh, 2004," Emerging Infectious Diseases vol. 11, No. 11: 1594-1597 (2005).*
(Continued)

*Primary Examiner* — Janet L Andres
*Assistant Examiner* — M. Franco Salvoza
(74) *Attorney, Agent, or Firm* — Henry D. Coleman; R. Neil Sudol

(57) ABSTRACT

The invention relates to virus-like particles of bacteriophage MS2 (MS2 VLPs) displaying peptide epitopes or peptide mimics of epitopes of Nipah Virus envelope glycoprotein that elicit an immune response against Nipah Virus upon vaccination of humans or animals. Affinity selection on Nipah Virus-neutralizing monoclonal antibodies using random sequence peptide libraries on MS2 VLPs selected peptides with sequence similarity to peptide sequences found within the envelope glycoprotein of Nipah itself, thus identifying the epitopes the antibodies recognize. The selected peptide sequences themselves are not necessarily identical in all respects to a sequence within Nipah Virus glycoprotein, and therefore may be referred to as epitope (Continued)

mimics VLPs displaying these epitope mimics can serve as vaccine. On the other hand, display of the corresponding wild-type sequence derived from Nipah Virus and corresponding to the epitope mapped by affinity selection, may also be used as a vaccine.

18 Claims, 6 Drawing Sheets

(51) Int. Cl.
    *A61K 49/00*     (2006.01)
    *A61K 39/385*     (2006.01)
    *C12Q 1/70*     (2006.01)
    *C12N 7/00*     (2006.01)
    *G01N 33/569*     (2006.01)

(56) References Cited

U.S. PATENT DOCUMENTS

| | | |
|---|---|---|
| 2011/0104203 A1 | 5/2011 | Peabody et al. |
| 2012/0295813 A1 | 11/2012 | Peabody et al. |
| 2012/0308592 A1 | 12/2012 | Peabody et al. |
| 2013/0017210 A1 | 1/2013 | Peabody et al. |
| 2013/0302371 A1 | 11/2013 | Peabody et al. |
| 2014/0105924 A1 | 4/2014 | Peabody et al. |
| 2014/0106982 A1 | 4/2014 | Peabody et al. |

FOREIGN PATENT DOCUMENTS

| | | | |
|---|---|---|---|
| WO | WO 2011082381 A2 * | 7/2011 | |
| WO | 2011100234 A2 | 8/2011 | |
| WO | 2011116226 A2 | 9/2011 | |
| WO | 2012037078 A2 | 3/2012 | |
| WO | 2013003353 A2 | 1/2013 | |
| WO | 2013063366 A2 | 5/2013 | |
| WO | 2013106525 A1 | 7/2013 | |

OTHER PUBLICATIONS

Lo et al., "Characterization of Nipah Virus from Outbreaks in Bangladesh, 2008-2010," Emerging Infectious Diseases, vol. 18, No. 2 (2012).*

Caldeira JC, et al. Immunogenic display of diverse peptides, including a broadly cross-type neutralizing human papillomavirus L2 epitope, on virus-like particles of the RNA bacteriophage PP7. Vaccine, 2010;28:4384-4393.

Chackerian B, et al. Peptide Epitope Identification by Affinity Selection on Bacteriophage MS2 Virus-Like Particles. J Mol Biol, 2011;409:225-237.

Peabody DS. Subunit Fusion Confers Tolerance to Peptide Insertions in a Virus Coat Protein. Biochemistry and Biophysics, 1997;347(1):85-92.

Peabody DS, et al. Immunogenic Display of Diverse Peptides on Virus-like Particles of RNA Phage MS2. J Mol Biol, 2008;380:252-263.

Strauss WM. Hybridization with Radioactive Probes. Current Protocols in Molecular Biology, 1993:6.3.1-6.3.6.

Beckett D, et al. Roles of Operator and Non-operator RNA Sequences in Bacteriophage R17 Capsid Assembly. J Mol Biol, 1988;204:939-947.

Peabody DS. Translational repression by bacteriophage MS2 coat protein expressed from a plasmid. A system for genetic analysis of a protein-RNA interaction. J Biol Chem, 1990;265:5684-5689.

Tatusova TA, Madden TL. BLAST 2 Sequences, a new tool for comparing protein and nucleotide sequences. FEMS Microbiology Letters, 1999;174:247-250.

* cited by examiner

| Clone | Sequence | ID Score | Round 1 | Round 2 | Round 3 | Round 4 |
|---|---|---|---|---|---|---|
| | | | (Frequency per 40 Sequenced Clones) | | | |
| A NiV | PEVCWEGVYNDA | | | | | |
| 1 | DIGWEGVYQA | 6.5 | 6 | 5 | 6 | 6 |
| 2 | LGWEAVYREA | 6.5 | 4 | 6 | 3 | 2 |
| 3 | GWDGVYQDSP | 6.0 | 1 | 1 | 0 | 0 |
| 4 | IGWDASYNEA | 6.0 | 1 | 0 | 0 | 0 |
| 5 | DSGWEGVYRQ | 5.5 | 6 | 8 | 18 | 28 |
| 6 | DLAWEGIYGK | 5.5 | 5 | 4 | 1 | 0 |
| 7 | DTGWDGVYQA | 5.5 | 4 | 6 | 3 | 0 |
| 8 | IGWEAVYKET | 5.5 | 2 | 1 | 1 | 0 |
| 9 | LAWDATYQEA | 5.5 | 0 | 1 | 0 | 0 |
| 10 | DVGWDGIFAE | 5.5 | 0 | 1 | 0 | 0 |
| 11 | ISFEGIYRQG | 5.0 | 1 | 0 | 0 | 0 |
| 12 | ADVAWDGIFA | 5.0 | 1 | 0 | 0 | 0 |
| 13 | TSWDAVYREH | 4.5 | 1 | 1 | 1 | 0 |
| 14 | SDVGWEASFA | 4.5 | 1 | 0 | 0 | 0 |
| 15 | DLSFEAAYQK | 4.5 | 1 | 0 | 0 | 0 |
| 16 | GWEASFARES | 3.0 | 0 | 1 | 0 | 0 |
| B NiV | FLDSNQTAENPVFTV | | | | | |
| 1 | GTNQTAENPI | 8 | 9 | 14 | 24 | 29 |
| 2 | GANQTAENPL | 7.5 | 7 | 6 | 7 | 4 |
| 3 | EANQTADNPI | 7.5 | 5 | 4 | 2 | 1 |
| 4 | EGNQTGENPL | 7.5 | 4 | 6 | 4 | 2 |
| 5 | GTNQTGENPA | 7 | 2 | 3 | 1 | 1 |
| 6 | TQQTGENPLG | 7 | 2 | 1 | 0 | 0 |
| 7 | TNQSGENPAS | 6.5 | 3 | 1 | 0 | 0 |
| 8 | ANQSADQPGK | 6 | 1 | 1 | 0 | 0 |
| 9 | GANNSADNPI | 6 | 1 | 0 | 0 | 0 |
| 10 | AANRTGENPG | 5.5 | 1 | 0 | 0 | 0 |
| C HeV | LAEDDTNAQKTI | | | | | |
| 1 | SATDDTNAQR | 7.5 | 5 | 8 | 9 | 4 |
| 2 | AADDTQAQKA | 7.5 | 4 | 4 | 1 | 2 |
| 3 | GDDTNAQRAF | 6.5 | 8 | 10 | 19 | 28 |
| 4 | TEDTNAQQGH | 5.5 | 6 | 7 | 3 | 2 |
| 5 | ADDTNSQRGY | 5.5 | 3 | 4 | 1 | 0 |
| 6 | GDESNSQNGI | 5 | 1 | 0 | 0 | 0 |
| 7 | GDETNGQGGW | 5 | 2 | 1 | 0 | 0 |
| 8 | PGEESNAQRA | 5 | 2 | 1 | 0 | 0 |
| 9 | AEDSNGRRSL | 5 | 1 | 0 | 0 | 0 |

Figure 2

AFFINITY SELECTION OF NIPAH AND HENDRA VIRUS-RELATED VACCINE CANDIDATES FROM A COMPLEX RANDOM PEPTIDE LIBRARY DISPLAYED ON BACTERIOPHAGE VIRUS-LIKE PARTICLES

The present application claims the benefit of priority of U.S. provisional application Ser. No. 61/727,389, of identical title, filed Nov. 16, 2012, the entire contents of which is incorporated by reference.

PRIORITY CLAIM AND GOVERNMENT INTEREST

This invention was made with government support under Grant Nos. R01 GM042901 and R01 AI08335 awarded by the National Institute of Health and Grant No. DE-AC04-94AL85000 awarded by the Department of Energy to Sandia Corporation. The government has certain rights in the invention.

FIELD OF THE INVENTION

The invention consists of bacteriophage MS2 virus-like particle vaccines for Nipah Virus. They were identified by affinity selection from complex random sequence peptide MS2 VLP libraries using monoclonal antibodies with neutralizing activity for Nipah virus.

BACKGROUND OF THE INVENTION

Nipah virus (NiV), a highly pathogenic member of the Paramyxoviridae family, was first isolated and identified after a 1998-1999 outbreak of fatal encephalitis among pig farmers and abattoir workers in Southeast Asia. NiV and its close relative, Hendra virus, have been classified as Biosafety Level 4 (BSL-4) select agents due to their broad host range, their numerous routes of transmission, and the high rates of mortality associated with infection. Despite recent advances in understanding the cellular tropism of NiV, there is currently no prophylaxis available for animals or humans, and treatment remains primarily supportive. Several DNA and virus-like particle (VLP)-based vaccines are under development and have been demonstrated to induce high-titer ($10^3$) antibody responses that protect various animal models against live NiV challenge. As an alternative approach, we are employing antibodies against NiV glycoprotein (NiV-G) to affinity-select peptide mimotopes from a complex random sequence library displayed on VLPs of MS2 bacteriophage.

Virus-like particles (VLPs) are derived from self-assembly of the structural proteins of a virus. Vaccines can be made from VLPs in two different ways. First, a vaccine against a given virus can be made from the structural proteins of that virus. In such cases, the VLP serves as a non-infectious version of the virus itself, and is utilized to safely elicit an antibody response to the virus from which it is derived. The existing vaccines for hepatitis B virus and human papilloma virus are examples. Second, VLPs can serve as scaffolds for the immunogenic presentation of epitopes derived from other sources (from whatever source, viral or not). The VLP-based vaccines described in this application are in this second category. There are made by the immunogenic presentation of Nipah Virus-derived epitopes on the surface of a VLP made by self-assembly of the coat protein of bacteriophage MS2 expressed from a plasmid in *E. coli*. In this case the VLP merely serves as a carrier to present a NiV epitope (or epitope mimic) to the immune system in an immunogenic format.

Because VLPs are structurally repetitious, linking target antigens, either genetically or chemically, to the VLP surface causes them to be displayed at high densities. Such densely-spaced repetitive elements provoke efficient oligomerization of the membrane-associated immunoglobulin (Ig) molecules that constitute the B cell receptor (BCR), which in turn promotes increased stimulation of the B cell. Thus, a normally non-immunogenic substance (e.g. a peptide) becomes strongly immunogenic when displayed as a dense repetitive array on a VLP. MS2 VLPs self-assemble from 180 copies of a single coat protein into a 28-nm icosahedron. The vaccines described here use a VLP assembled from a single-chain coat protein dimer, and can display up to 90 peptides per particle in a highly accessible surface loop. Thus presented, peptide epitopes, are able to elicit high titer antibody responses in immunized animals or humans, even though they are very poorly immunogenic on their own. MS2 VLPs are, furthermore, highly tolerant of random peptide insertions and encapsidate the mRNA that encodes the coat protein-random peptide fusion, enabling their development as a display platform for a wide range of different peptide sequences, and enabling the construction of random peptide libraries from which specific epitope mimics can be isolated by affinity-selection on antibody targets. In addition to its dependence on the ability to tolerate a wide variety of different peptide insertions, affinity-selection also takes advantage of the fact that the VLP encapsidates the mRNA that encodes it and any guest peptide it carries, thus allowing the recovery of affinity-selected sequences by reverse transcription and PCR amplification.

We have employed complex (~$10^{10}$ members), random peptide (10 amino acids in length) libraries to affinity-select MS2 VLPs that bind to neutralizing monoclonal antibodies against NiV-G. After two rounds of selection at high valency (90 peptides/VLP) and two rounds at low valency (~3 peptides/VLP), we obtained peptides for each antibody that map directly onto the NiV-G sequence. VLPs that display a high density (90 copies/VLP) of these peptides bind to their respective antibodies with high affinity ($K_d$=1-20 nM). Immunization of mice with the resulting VLPs elicits antibodies that neutralize infection by a Nipah G-protein pseudotyped vesicular stomatitis virus (a surrogate for Nipah Virus itself).

SUMMARY OF THE INVENTION

In one embodiment, the invention provides a nucleic acid construct comprising:
(a) a bacterial or bacteriophage promoter which is operably associated with a coding sequence of bacteriophage single chain coat polypeptide dimer, wherein the coat polypeptide dimer coding sequence is modified to define a peptide-encoding sequence in that portion of the sequence which defines the coat polypeptide dimer AB loop;
(b) a nucleotide sequence which encodes a Nipah or Hendra Virus peptide epitope recognized by a Nipah or Hendra virus-neutralizing antibody, or (c) a nucleotide sequence which encodes a peptide mimic of an epitope recognized by a Nipah or Hendra Virus-neutralizing antibody.

The examples described hereinafter relate to NiV, but the scope of our invention includes the closely-related Hendra virus (HeV), since many of HeV's epitopes have identical or substantially similar amino acid sequences as those of Nipah virus (NiV). The affinity-selected sequences, as well as the corresponding wild-type sequences in G-protein are also useful as potential vaccines. In most selections, we encountered some sequences that lack obvious similarity to the G-protein sequence itself. Such peptides could represent immunogenic mimics of NiV epitopes and should also be considered as being within the scope of the invention as useful vaccine candidates.

Related viral-like particles, methods for constructing a library of VLPs, immunogenic compositions, drug delivery vehicles comprising one or more pharmaceutically-active ingredients, methods for inducing an immune response in a mammal, vaccines comprised of VLPs as described herein, VLP libraries, assays and kits are also provided.

These and other aspects of the invention are described further in the Detailed Description of the Invention.

BRIEF DESCRIPTION OF THE FIGURES

FIG. 2. Peptide sequences obtained after a random 10-mer library displayed on MS2 VLPs were subjected to four rounds of affinity selection against $mAb_{500}$ (A), $mAb_{525}$ (B), or $mAb_{551}$ (C). For each affinity-selected peptide, residues that are identical to the wild-type epitope are in bold, and chemically similar residues are in italics; bold residues in the wild-type NiV and HeV epitopes denote the consensus sequence that resulted from the corresponding selection. Each affinity-selected sequence was given an identity (ID) score based upon similarity to NiV-G ($mAb_{500}$ and $mAb_{525}$ selectants) or HeV-G ($mAb_{551}$ selectants); 1 point was given for each identical amino acid residue, and 0.5 points were given for each chemically similar amino acid residue and 0 point were given for each dissimilar amino acid residue. By way of example, amino acids which are similar are those amino acids having similar physicochemical characteristics, such as glutamic acid and aspartic acid or valine, leucine and isoleucine.

DETAILED DESCRIPTION OF THE INVENTION

Figure 1:
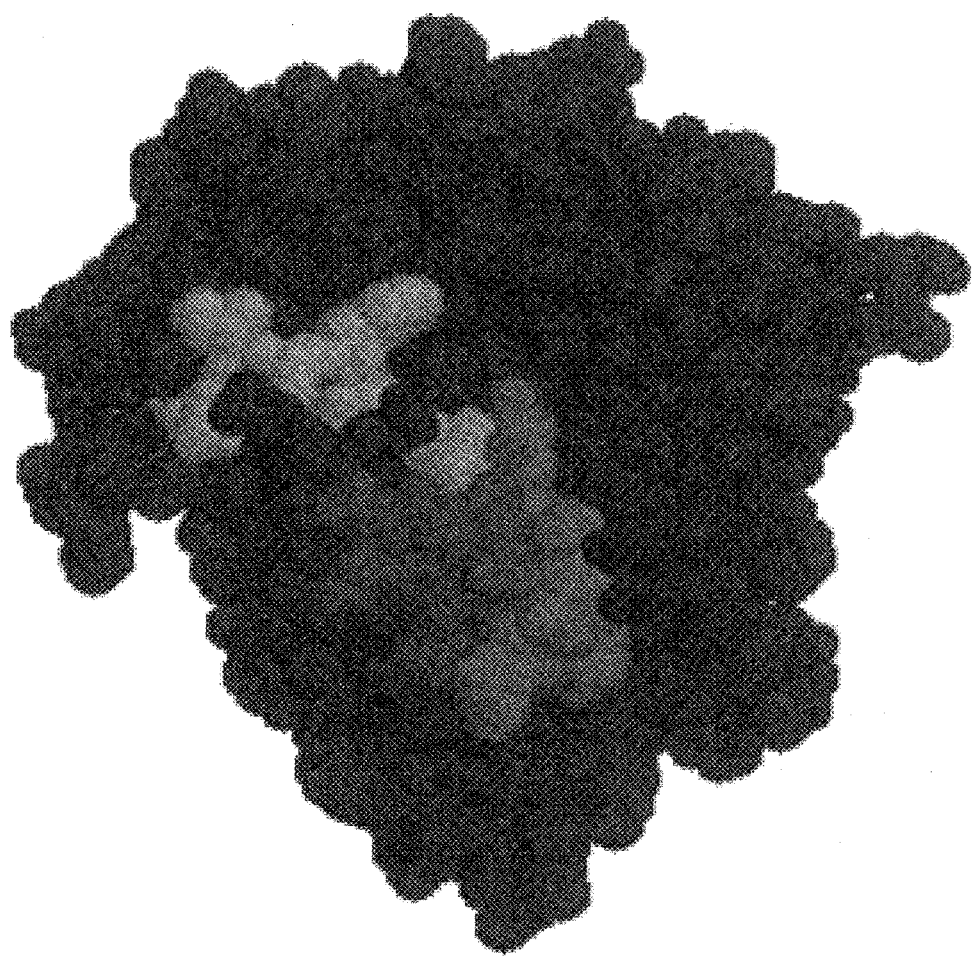
FIG. 1 depicts the locations of the mapped epitopes on the 3D structure of the NiV G-protein. This view roughly looks down on the site where G-protein binds its receptor on the cell surface. The $mAb_{500}$ epitope is in light gray, the $mAb_{525}$ epitope is in dark gray and the $mAb_{551}$ epitope is in gray.

In accordance with the present invention there may be employed conventional molecular biology, microbiology, and recombinant DNA techniques within the skill of the art. Such techniques are explained fully in the literature. See, e.g., Sambrook et al, 2001, "Molecular Cloning: A Laboratory Manual"; Ausubel, ed., 1994, "Current Protocols in Molecular Biology" Volumes I-III; Celis, ed., 1994, "Cell Biology: A Laboratory Handbook" Volumes I-III; Coligan, ed., 1994, "Current Protocols in Immunology" Volumes I-III; Gait ed., 1984, "Oligonucleotide Synthesis"; Hames & Higgins eds., 1985, "Nucleic Acid Hybridization"; Hames & Higgins, eds., 1984, "Transcription And Translation"; Freshney, ed., 1986, "Animal Cell Culture"; IRL Press, 1986, "Immobilized Cells And Enzymes"; Perbal, 1984, "A Practical Guide To Molecular Cloning."

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It must be noted that as used herein and in the appended claims, the singular forms "a," "and" and "the" include plural references unless the context clearly dictates otherwise.

Furthermore, the following terms shall have the definitions set out below.

As used herein, the term "polynucleotide" refers to a polymeric form of nucleotides of any length, either ribonucleotides or deoxynucleotides, and includes both double- and single-stranded DNA and RNA. A polynucleotide may include nucleotide sequences having different functions, such as coding regions, and non-coding regions such as regulatory sequences (e.g., promoters or transcriptional terminators). A polynucleotide can be obtained directly from a natural source, or can be prepared with the aid of recombinant, enzymatic, or chemical techniques. A polynucleotide can be linear or circular in topology. A polynucleotide can be, for example, a portion of a vector, such as an expression or cloning vector, or a fragment.

As used herein, the term "polypeptide" refers broadly to a polymer of two or more amino acids joined together by peptide bonds. The term "polypeptide" also includes molecules which contain more than one polypeptide joined by a disulfide bond, or complexes of polypeptides that are joined together, covalently or noncovalently, as multimers (e g., dimers, tetramers). Thus, the terms peptide, oligopeptide, and protein are all included within the definition of polypeptide and these terms are used interchangeably. It should be understood that these terms do not connote a specific length of a polymer of amino acids, nor are they intended to imply or distinguish whether the polypeptide is produced using recombinant techniques, chemical or enzymatic synthesis, or is naturally occurring.

The amino acid residues described herein are preferred to be in the "L" isomeric form. However, residues in the "D" isomeric form can be substituted for any L-amino acid residue, as long as the desired functional is retained by the polypeptide. $NH_2$ refers to the free amino group present at the amino terminus of a polypeptide. COOH refers to the free carboxy group present at the carboxy terminus of a polypeptide.

The term "coding sequence" is defined herein as a portion of a nucleic acid sequence which directly specifies the amino acid sequence of its protein product. The boundaries of the coding sequence are generally determined by a ribosome binding site (prokaryotes) or by the ATG start codon (eukaryotes) located just upstream of the open reading frame at the 5'-end of the mRNA and a transcription terminator sequence located just downstream of the open reading frame at the 3'-end of the mRNA. A coding sequence can include, but is not limited to, DNA, cDNA, and recombinant nucleic acid sequences.

A "heterologous" region of a recombinant cell is an identifiable segment of nucleic acid within a larger nucleic acid molecule that is not found in association with the larger molecule in nature.

An "origin of replication" refers to those DNA sequences that participate in DNA synthesis.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation, as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgarno sequences in addition to the −10 and −35 consensus sequences.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence. Transcriptional and translational control sequences are DNA regulatory sequences, such as promoters, enhancers, polyadenylation signals, terminators, and the like, that provide for the expression of a coding sequence in a host cell.

A "signal sequence" can be included before the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

A cell has been "transformed" by exogenous or heterologous DNA when such DNA has been introduced inside the cell. The transforming DNA may or may not be integrated (covalently linked) into chromosomal DNA making up the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA.

It should be appreciated that also within the scope of the present invention are nucleic acid sequences encoding the polypeptide(s) of the present invention, which code for a polypeptide having the same amino acid sequence as the sequences disclosed herein, but which are degenerate to the nucleic acids disclosed herein. By "degenerate to" is meant that a different three-letter codon is used to specify a particular amino acid.

As used herein, "epitope" refers to an antigenic determinant of a polypeptide. An epitope could comprise 3 amino acids in a spatial conformation which is unique to the epitope. Generally an epitope consists of at least 5, 6 or 7 such amino acids, and more usually, consists of at least 8, 9 or 10 such amino acids. Methods of determining the spatial conformation of amino acids are known in the art, and include, for example, x-ray crystallography and 2-dimensional nuclear magnetic resonance.

In the present invention, preferred epitopic peptide sequences for inclusion into VLPs according to the present invention include those which are set forth in attached FIG. 2. Alternatively, any peptide which comprises at least 5, 6, 7, 8 or 9 contiguous amino acids (preferably, such a peptide will contain 6, 7, 8, 9, 10, 11, 12, 13, 14 or up to about 15 amino acids), corresponding to any one of the peptides which are listed in FIG. 2 are also epitopic peptide sequences which may be included in VLPs according to the present invention in order to provide an immunogenic composition and generate an immunogenic response in a patient. In addition to the above, any 10 mer peptide having an ID Score as defined herein of at least 3.0 when compared to the wild-type sequence (labeled NiV or HeV) in FIG. 2 are also useful as epitopic peptide sequences for inclusion into VLPs according to the present invention. By way of example, the identity (ID) score of a peptide is based upon similarity to NiV-G ($mAb_{500}$ and $mAb_{525}$ selectants) or HeV-G ($mAb_{551}$ selectants) as set forth and identified in FIG. 2; 1 point being given for each identical amino acid residue, and 0.5 points given for each chemically similar amino acid residue and 0 point being given for each dissimilar amino acid residue. By way of example, amino acids which are similar are those amino acids having similar physicochemical characteristics, such as glutamic acid and aspartic acid or valine, leucine and isoleucine. Preferred peptide sequences for inclusion into VLPs as heterologous peptides correspond to 10 mer peptides having an ID score of at least about 3.0, 3.5, 4.0, 4.5, 5.0, 5.5, 6.0, 6.5, 7.0, 7.5, 8.0, 8.5, 9.0 or 9.5 with preferred peptides having an ID score which is closer to 10 (based upon the NiV-G ($mAb_{500}$ and $mAb_{525}$ selectants) or HeV-G ($mAb_{551}$ selectants)) as set forth and identified in FIG. 2.

As used herein, a "mimotope" is a peptide or a carbohydrate that mimics an authentic antigenic epitope.

As used herein, the term "coat protein(s)" refers to the protein(s) of a bacteriophage or a RNA-phage capable of being incorporated within the capsid assembly of the bacteriophage or the RNA-phage.

As used herein, a "coat polypeptide" as defined herein is a polypeptide fragment of the coat protein that possesses coat protein function and additionally encompasses the full length coat protein as well or single-chain variants thereof.

As used herein, the term "immune response" refers to a humoral immune response and/or cellular immune response leading to the activation or proliferation of B- and/or T-lymphocytes and/or and antigen presenting cells. In some instances, however, the immune responses may be of low intensity and become detectable only when using at least one substance in accordance with the invention. "Immunogenic" refers to an agent used to stimulate the immune system of a living organism, so that one or more functions of the immune system are increased and directed towards the immunogenic agent. An "immunogenic polypeptide" is a polypeptide that elicits a cellular and/or humoral immune response, whether alone or linked to a carrier in the presence or absence of an adjuvant. Preferably, antigen presenting cell may be activated.

As used herein, the term "self antigen" refers to proteins encoded by the host's DNA and products generated by proteins or RNA encoded by the host's DNA are defined as self. In addition, proteins that result from a combination of two or several self-molecules or that represent a fraction of a self-molecule and proteins that have a high homology two self-molecules as defined above (>95%, preferably >97%, more preferably >99%) may also be considered self. Examples of a self-antigen includes but is not limited to ErbB-2, amyloid-beta, immunoglubulin E (IgE), gastrin, ghrelin, vascular endothelial growth factor (VEGF), interleukin (IL)-17, IL-23, IL-13, CCR5, CXCR4, nerve growth factor (NGF), angiotensin II, TRANCE/RANKL and MUC-1.

As used herein, the term "vaccine" refers to a formulation which contains the composition of the present invention and which is in a form that is capable of being administered to an animal to generate an immunogenic response consistent with reducing the likelihood of disease in the animal which has been vaccinated. The term "subject" or "patient" is used to describe an animal, preferably a mammal, including a domesticated animal (most likely a horse) or a human to whom vaccines or immunogenic compositions according to the present invention are administered.

The term "effective" is used to describe an amount or concentration of a composition, component, intermediate, compound, construct, etc. (including over an appropriate period of time) that when used, produces an intended effect.

As used herein, the term "virus-like particle of a bacteriophage" refers to a virus-like particle (VLP) resembling the structure of a bacteriophage, being non replicative and noninfectious, and lacking at least the gene or genes encoding for the replication machinery of the bacteriophage, and typically also lacking the gene or genes encoding the protein or proteins responsible for viral attachment to or entry into the host. This definition should, however, also encompass virus-like particles of bacteriophages, in which the aforementioned gene or genes are still present but inactive, and, therefore, also leading to non-replicative and noninfectious virus-like particles of a bacteriophage.

VLP of RNA bacteriophage coat protein: The capsid structure formed from the self-assembly of one or more subunits of RNA bacteriophage coat protein and optionally containing host RNA is referred to as a "VLP of RNA bacteriophage coat protein". For example, in a particular embodiment, the capsid structure is formed from the self assembly of 1-180 subunits.

A nucleic acid molecule is "operatively linked" to, or "operably associated with", an expression control sequence when the expression control sequence controls and regulates the transcription and translation of nucleic acid sequence. The term "operatively linked" includes having an appropriate start signal (e.g., ATG) in front of the nucleic acid sequence to be expressed and maintaining the correct reading frame to permit expression of the nucleic acid sequence under the control of the expression control sequence and production of the desired product encoded by the nucleic acid sequence. If a gene that one desires to insert into a recombinant DNA molecule does not contain an appropriate start signal, such a start signal can be inserted in front of the gene.

The term "stringent hybridization conditions" are known to those skilled in the art and can be found in Current Protocols in Molecular Biology, John Wiley & Sons, N.Y. (1989), 6.3.1-6.3.6. A preferred, non-limiting example of stringent hybridization conditions is hybridization in 6× sodium chloride/sodium citrate (SSC) at about 45° C., followed by one or more washes in 0.2.×SSC, 0.1% SDS at 50° C., preferably at 55° C., and more preferably at 60° C. or 65° C.

The Hendra and Nipah Viruses (HeV and NiV, respectively) are recently emerged zoonotic pathogens of the family Paramyxoviridae. Found naturally in bats, they have a wide host range and can infect humans as well as a number of other animal species. Hendra was discovered in Australia in 1994 when it killed 13 horses and their human trainer near Brisbane, Australia. The closely related virus called Nipah appeared in 1999 as an infection of pigs in Malaysia. It resulted in the culling of about a million pigs, but is known also to have caused 257 human infections, 105 of them resulting in death. The henipaviruses are considered important emerging natural pathogens and potential bioweapons.

Both viruses are characterized by a pleomorphic, enveloped virion ranging in size from 40 to 600 nm, and containing a single-stranded negative sense RNA genome about 18.2 kb in length. The lipid envelope is decorated with an attachment protein (called G-protein) and a fusion protein (the F-protein). The literature reports the isolation of a number of monoclonal antibodies capable of neutralizing NiV through binding of the G-protein. We determined the epitopes recognized by four such antibodies by conducting affinity selection using random sequence peptide libraries displayed on MS2 VLPs. This technology for mapping epitopes, and for their immunogenic presentation as a vaccine on the MS2 platform have been extensively described elsewhere [1-4]. The work described here concentrated on NiV, but our results also have implications for the closely related HeV, since many of the epitopes have identical, or highly similar amino acid sequences. Thus a vaccine for Nipah may also serve for Hendra.

Production of Virus-Like Particles

The present invention utilized random sequence peptide libraries displayed on VLPs of bacteriphage MS2 to find Nipah virus vaccine epitopes and epitope mimics by affinity selection on Nipah Virus-neutralizing antibodies. The VLPs are normally produced by genetic expression from plasmids in *E. coli*, although production by coupled transcription/translation in vitro is also possible.

Bacteriophages

Systems used herein are based on VLPs produced by expression (usually from plasmids in *E. coli*) of the coat protein of RNA bacteriophage MS2. The properties and characteristics of single-strand RNA bacteriophages are presented in: RNA Bacteriophages, in The Bacteriophages. Calendar, R L, ed. Oxford University Press. 2005). The known viruses of this group attack bacteria as diverse as *E. coli, Pseudomonas* and *Acinetobacter*. Each possesses a highly similar genome organization, replication strategy, and virion structure. In particular, the bacteriophages contain a single-stranded (+)-sense RNA genome, contain maturase, coat and replicase genes, and have small (<300 angstrom) icosahedral capsids. These include but are not limited to MS2, Qb, R17, SP, PP7, GA, M11, MX1, f4, Cb5, Cb12r, Cb23r, 7s and f2 RNA bacteriophages. These other bacteriophages may also be used in the present invention, more likely PP7 and MS2, most likely MS2.

For background information and for purposes of illustration, the genome of a particularly well-characterized member of the group, called MS2, comprises a single strand of (+)-sense RNA 3569 nucleotides long, encoding only four proteins, two of which are structural components of the virion. The viral particle is comprised of an icosahedral capsid made of 180 copies of coat protein and one molecule of maturase protein together with one molecule of the RNA genome. Coat protein is also a specific RNA binding protein. Assembly may possibly be initiated when coat protein associates with its specific recognition target an RNA hairpin near the 5'-end of the replicase cistron. The virus particle is then liberated into the medium when the cell bursts under the influence of the viral lysis protein. The formation of an infectious virus requires at least three components, namely coat protein, maturase and viral genome RNA, but experiments show that the information required for assembly of the icosahedral capsid shell is contained entirely within coat protein itself. For example, purified coat protein can form capsids in vitro in a process stimulated by the presence of RNA [Beckett et al., 1988, J. Mol Biol 204: 939-47]. Moreover, coat protein expressed in cells from a plasmid assembles into a virus-like particle in vivo [Peabody, D. S., 1990, J Biol Chem 265: 5684-5689]. It is not the MS2 virus itself, but rather these virus-like particles (or VLPs) that form the basis of the present invention Coat Polypeptide The coat polypeptide encoded by the coding region is typically at least 120, preferably, at least 125 amino acids in length, and no greater than 135 amino acids in length, preferably, no greater than 130 amino acids in length. Although the VLPs described in the present invention are derived from MS2, it is expected that a coat polypeptide from essentially any single-stranded RNA bacteriophage can be used. Examples of coat polypeptides include but are not limited to the MS2 coat polypeptide, R17 coat polypeptide (see, for example, Genbank Accession No P03612), PRR1 coat Polypeptide (see, for example, Genbank Accession No. ABH03627), for phage coat polypeptide (see, for example, Genbank Accession No. NP_039624), GA coat polypeptide (see, for example, Genbank Accession No. P07234), Qb coat polypeptide (See, for example, Genbank Accession No. P03615), SP coat polypeptide (see, for example, Genbank Accession No P09673), f4 coat polypeptide (see, for example, Genbank accession no. M37979.1 and PP7 coat polypeptide (see, for example, Genbank Accession No P03630).

The coat polypeptides useful in the present invention also include those having similarity with one or more of the coat polypeptide sequences disclosed above. The similarity is referred to as structural similarity. Structural similarity may be determined by aligning the residues of the two amino acid sequences (i.e., a candidate amino acid sequence and the amino acid sequence) to optimize the number of identical amino acids along the lengths of their sequences; gaps in either or both sequences are permitted in making the alignment in order to optimize the number of identical amino acids, although the amino acids in each sequence must nonetheless remain in their proper order. A candidate amino acid sequence can be isolated from a single stranded RNA virus, or can be produced using recombinant techniques, or chemically or enzymatically synthesized. Preferably, two amino acid sequences are compared using the BESTFIT algorithm in the GCG package (version 10.2, Madison Wis.), or the Blastp program of the BLAST 2 search algorithm, as described by Tatusova, et al. (*FEMS Microbial Lett* 1999, 174:247-250), and available at the website ncbi.nlm.nih.gov/blast/bl2seq/bl2.html. Preferably, the default values for all BLAST 2 search parameters are used, including matrix=BLOSUM62; open gap penalty=11, extension gap penalty=1, gap xdropoff=50, expect=10, wordsize=3, and optionally, filter on. In the comparison of two amino acid sequences using the BLAST search algorithm, structural similarity is referred to as "identities." Preferably, a coat polypeptide also includes polypeptides with an amino acid sequence having at least 80% amino acid identity, at least 85% amino acid identity, at least 90% amino acid identity, or at least 95% amino acid identity to one or more of the amino acid sequences disclosed above. Preferably, a coat polypeptide is active. Whether a coat polypeptide is active can be determined by evaluating the ability of the polypeptide to form a capsid and package a single stranded RNA molecule. Such an evaluation can be done using an in vivo or in vitro system, and such methods are known in the art and routine. Alternatively, a polypeptide may be considered to be structurally similar if it has similar three dimensional structure as the recited coat polypeptide and/or functional activity.

In order to determine a corresponding position in a structurally similar coat polypeptide, the amino acid sequence of this structurally similar coat polypeptide is aligned with the sequence of the named coat polypeptide as specified above.

In a particular embodiment, the coat polypeptide is a single-chain dimer containing an upstream and downstream subunit. Each subunit contains a functional coat polypeptide sequence. The peptide epitope is inserted into the AB-loop of the downstream copy of a single chain dimer of an MS2 coat polypeptide.

Preparation of Transcription Unit

The transcription unit of the present invention comprises an expression regulatory region, (e.g., a promoter), a sequence encoding a coat polypeptide and a transcription terminator. The RNA polynucleotide may optionally include a coat recognition site (also referred to a "packaging signal", "translational operator sequence", "coat recognition site"). Alternatively, the transcription unit may be free of the translational operator sequence. The promoter, coding region, transcription terminator, and, when present, the coat recognition site, are generally operably linked.

"Operably linked" or "operably associated with" refer to a juxtaposition wherein the components so described are in a relationship permitting them to function in their intended manner. A regulatory sequence is "operably linked" to, or "operably associated with", a coding region when it is joined in such a way that expression of the coding region is achieved under conditions compatible with the regulatory sequence. The coat recognition site, when present, may be at any location within the RNA polynucleotide provided it functions in the intended manner.

The invention is not limited by the use of any particular promoter, and a wide variety of promoters are known. The promoter used in the invention can be a constitutive or an inducible promoter. Preferred promoters are able to drive high levels of RNA encoded by me coding region encoding the coat polypeptide Examples of such promoters are known in the art and include, for instance, T7, T3, and SP6 promoters.

The nucleotide sequences of the coding regions encoding coat polypeptides described herein are readily determined. These classes of nucleotide sequences are large but finite, and the nucleotide sequence of each member of the class can be readily determined by one skilled in the art by reference to the standard genetic code.

Furthermore, the coding sequence of an RNA bacteriophage single chain coat polypeptide comprises a site for insertion of a heterologous peptide as well as a coding sequence for the heterologous peptide itself. In a particular embodiment, the site for insertion of the heterologous peptide is a restriction enzyme site.

In a particular embodiment, the coding region encodes a single-chain dimer of the coat polypeptide. In a most particular embodiment, the coding region encodes a modified single chain coat polypeptide dimer, where the modification comprises an insertion of a coding sequence at least four amino acids at the insertion site. The transcription unit may contain a bacterial promoter, such as a lac promoter or it ma contain a bacteriophage promoter, such as a T7 promoter and optionally a T7 transcription terminator.

In addition to containing a promoter and a coding region encoding a fusion polypeptide, the RNA polynucleotide typically includes a transcription terminator, and optionally, a coat recognition site. A coat recognition site is a nucleotide sequence that forms a hairpin when present as RNA. This is also referred to in the art as a translational operator, a packaging signal, and an RNA binding site. Without intending to be limiting, this structure is believed to act as the binding site recognized by the translational repressor (e.g., the coat polypeptide), and initiate RNA packaging. The nucleotide sequences of coat recognition sites are known in the art. Other coat recognition sequences have been characterized in the single stranded RNA bacteriophages R17, GA, Qβ, SP, and PP7, and are readily available to the skilled person. Essentially any transcriptional terminator can be used in the RNA polynucleotide, provided it functions with the promoter. Transcriptional terminators are known to the skilled person, readily available, and routinely used.

Synthesis

VLPs are normally produced by expression from plasmids in *E. coli*, but could be produced in vitro in a coupled cell-free transcription/translation system.

Immunogenic Compositions

As noted above, the VLPs identified by the screening procedures of the present invention may be used to formulate immunogenic compositions, particularly vaccines. The vaccines should be in a form that is capable of being administered to an animal. Typically, the vaccine comprises a conventional saline or buffered aqueous solution medium in which the composition of the present invention is suspended or dissolved. In this form, the composition of the present invention can be used conveniently to prevent, ameliorate, or otherwise treat a condition or disorder. Upon introduction into a host, the vaccine is able to provoke an immune response including, but not limited to, the production of antibodies and/or cytokines and/or the activation of cytotoxic T cells, antigen-presenting cells, helper T cells, dendritic cells and/or other cellular responses.

A vaccine of the present invention may also include an adjuvant, which can be present in either a minor or major proportion relative to the compound of the present invention. The term "adjuvant" as used herein refers to non-specific stimulators of the immune response or substances that allow generation of a depot in the host which when combined with the vaccine of the present invention provide for an even more enhanced immune response. A variety of adjuvants can be used. Examples include complete and incomplete Freund's adjuvant, aluminum hydroxide and modified muramyl dipeptide.

Optionally, a vaccine of the present invention additionally includes an adjuvant which can be present in either a minor or major proportion relative to the compound of the present invention.

Example 1

NiV Epitope Mapping Data

As discussed above, the literature reports the isolation of a number of monoclonal antibodies capable of neutralizing NiV through binding of the G-protein. We determined the epitopes recognized by four such antibodies by conducting affinity selection using random sequence peptide libraries displayed on MS2 VLPs. This technology for mapping epitopes, and for their immunogenic presentation as a vaccine on the MS2 platform have been extensively described elsewhere [1-4]. The work described here concentrated on NiV, but our results also have implications for the closely related HeV, since many of the epitopes have identical, or highly similar amino acid sequences. Thus a vaccine for Nipah may also serve for Hendra.

The affinity-selected sequences, as well as the corresponding G-protein wild-type sequences are potential vaccines. In most selections we encountered some sequences that lack obvious similarity to the G-protein sequence itself. Such peptides could represent immunogenic mimics of NiV epitopes and should also be considered as vaccine candidates, but since some occur independently in different selections are likely artifacts generated by binding to plastic, or to some common part of the antibodies outside their antigen-binding sites.

The Selecting Antibodies and their Sources:

$mAb_{525}$
Mouse monoclonal against NiV-G; produced originally by the inventors by immunization with FLDSNQTAENPVFTV (SEQ ID NO: 18) (aa 525-539) linked to a carrier protein.
$IC_{90}$=0.2 nM
Competes with ephrin B2 and ephrin B3

$mAb_{500}$
Mouse monoclonal against NiV-G; produced by the inventors via immunization with PEVCWEGVYNDA (SEQ ID NO: 1) (aa 500-511) linked to a carrier protein.
$IC_{90}$=350 nM
Competes with ephrin B3 (and ephrin B2 to a lesser extent)

$mAb_{551}$
Mouse monoclonal against HeV-G (and NiV-G); produced by the inventors via immunization with LASEDTNAQKTI (SEQ ID NO: 45) (aa 551-562) linked to a carrier protein.
$IC_{90}$=12 nM
Competes with ephrin B2

Affinity Selection—

Each of the monoclonal antibodies was adsorbed to the plastic surface of a well in a 96-well plate and then incubated with a 10-fold molar excess of a random sequence peptide 10-mer library displayed in the MS2 coat protein AB-loop. The library has a complexity of about $2 \times 10^{10}$ individual members. VLPs that bound the antibody were eluted and the RNA they contain was subjected to reverse transcription and polymerase chain reaction. The resulting DNA product was cloned for expression of the first round selectants. A total of four rounds of selection were conducted in most cases, the first two at high-valency (i.e. 90/VLP) and the last two rounds at low valency (~3/VLP). Twenty clones from each mAb selection were subjected to DNA sequence analysis.

We present below a summary of the epitope mapping data, and describe:
1. the following sequences of the most abundant peptides found in the affinity-selected VLP population, with amino acid identities to the natural sequence shown in bold;
2. their alignment with a segment of the wild-type G-protein sequence (shown directly below such sequence).

Note that many related peptides are encountered in early rounds of selection by each antibody. These VLPs also represent potential vaccine immunogens. For simplicity we list the predominant selectants below, but the additional sequences are shown in FIG. 2.

$mAb_{525}$
GTNQTAENPI (VLP) (SEQ ID NO: 19)
DSNQTAENPV (G-protein) (SEQ ID NO: 139)

$mAb_{500}$
DSGWEGVYRQ (VLP) (SEQ ID NO: 6)
EVCWEGVYND (G-protein) (SEQ ID NO: 42)

$MAb_{551}$
GDDTNAQRAF (VLP) (SEQ ID NO: 32)
SEDTNAQKTI (G-protein) (SEQ ID NO: 43)

The sequence below is the amino acid sequence of NiV G-protein with the residues of the newly mapped epitopes highlighted in bold:

(SEQ ID NO: 44)
MPAENKKVRFENTTSDKGKNPSKVIKSYYGTMDIKKINEGLLDSKILSAFN

TVIALLGSIVIIVMNIMIIQNYTRSTDNQAVIKDALQGIQQQIKGLADKIG

TEIGPKVSLIDTSSTITIPANIGLLGSKISQSTASINENVNEKCKFTLPPL

KIHECNISCPNPLPFREYRPQTEGVSNLVGLPDNICLQKTSNQILKPKLIS

YTLPVVGQSGTCITDPLLAMDEGYFAYSHLERIGSCSRGVSKQRIIGVGEV

LDRGDEVPSLFMTNVWTPPNPNTVYHCSAVYNNEFYYVLCAVSTVGDPILN

STYWSGSLMMTRLAVKPKSNGGGYNQHQLALRSIEKGRYDKVMPYGPSGIK

QGDTLYFPAVGFLVRTEFKYNDSNCPITKCQYSKPENCRLSMGIRPNSHYI

LRSGLLKYNLSDGENPKIVFIEISDQRLSIGSPSKVYDSLGQPVFYQASFS

WDTMIKFGDVQTVNPLVVNWRDNTVISRPGQSQCPRFNTCPEICWEGVYND

AFLIDRINWISAGVFLDSNQTAENPVFTVFKDNEILYRAQLASEDTNAQKT

ITNCFLLKNKIWCISLVEIYDTGDNVIRPKLFAVKIPEQCT

FIG. 1 illustrates the locations of the mapped epitopes on the 3D structure of the NiV G-protein. This view roughly looks down on the site where G-protein binds its receptor on the cell surface.

$mAb_{525}$—dark gray (amino acids 529-535)
$mAb_{500}$—light gray (amino acids 504-508)
$mAb_{551}$—gray (amino acids 554-560)

FIG. 2 summarizes more fully the results of affinity-selection by showing the sequences of the major selectants present after each of four rounds of selection, and their similarities to a corresponding sequence within the NiV-G protein amino acid sequence. From these data one can follow the progress of selection. Each of these VLPs represents a potential vaccine immunogen. Other epitopes which can be incorporated as peptides into the VLPs as immunogenic compounds are readily identified pursuant to the present invention.

Example 2

NiV VLPs

Immunizations and Neutralization Assays.

Here we report the testing of VLP selectants from each of the antibodies for immunogenicity and for their ability to elicit neutralizing antibodies in mice. The neutralization assay utilizes a NiV-VSV pseudotype, i.e. a recombinant Vesicular Stomatitis Virus with the NiV atglycoprotein (which is responsible for viral attachment and fusion) on its surface. This means that infection of cells in culture by the pseudotype is mediated by the interaction of Nipah G-protein with the Ephrin B2 (and/or Ephrin B3) receptor. The pseudotype virus also carries a luciferase gene, so infection results in production of light, which can be measured in a luminometer as Relative Luminescence Units (RLU). The results show that the VLPs elicited an easily detected antibody response to Nipah G-protein in ELISA.

Figure 3:
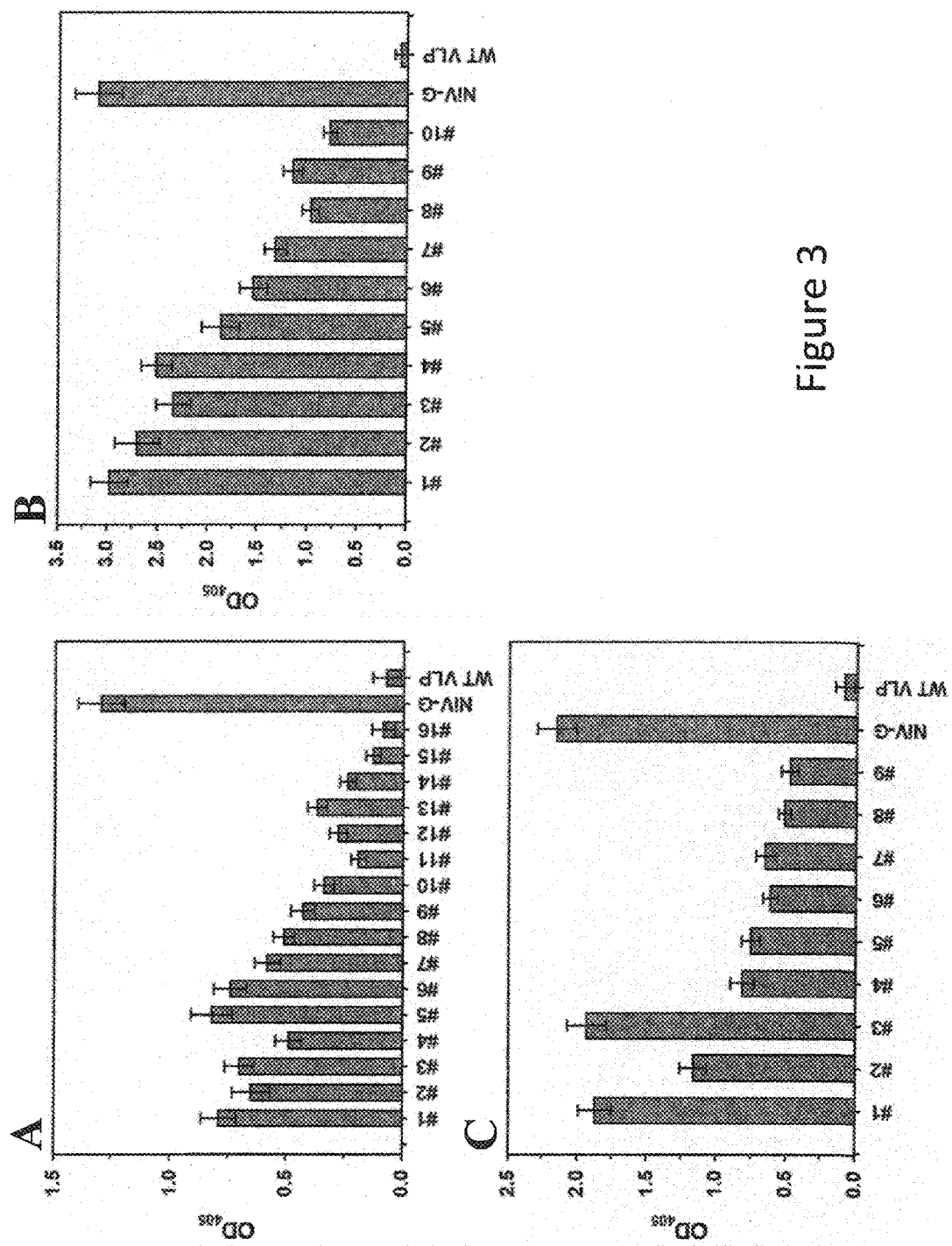
FIG. 3. ELISA showing binding of affinity-selected VLPs to $mAb_{500}$ (A), $mAb_{525}$ (B), and $mAb_{551}$ (C). $mAb_{500}$, $mAb_{525}$, and $mAb_{551}$ were adsorbed to Immulon 4 HBX 96-well plates overnight at 4° C. and then incubated with individual affinity-selected VLPs, soluble NiV-G fused to the Fc domain from human IgG, or wild-type VLPs ('WT VLP') for 1 hour at 37° C. Plates were washed extensively with 1×PBS and then serially incubated with a rabbit polyclonal antibody against either MS2 coat protein or human IgG and a horseradish peroxidase (HRP)-conjugated goat polyclonal antibody against rabbit IgG for 1 hour at 37° C. Plates were then washed three times with 1×PBS, incubated with 2,2'-Azinobis [3-ethylbenzothiazoline-6-sulfonic acid]-diammonium salt (ABTS) for 20 minutes at room temperature, and read at 405-nm. Error bars represent the mean+/−the standard deviation for n=3. See FIG. 2 for the peptide sequences that correspond to the clone numbers given on the x-axis of each plot.

FIG. 3 illustrates ELISA data showing the ability of sera of mice immunized with various VLPs to recognize recombinant Nipah G-protein. Three animals were immunized with each of the VLPs and the sera were pooled for this assay. NG2 and NG6 are the VLPs selected by mAb$_{525}$ and mAb$_{551}$, respectively.

Figure 4:
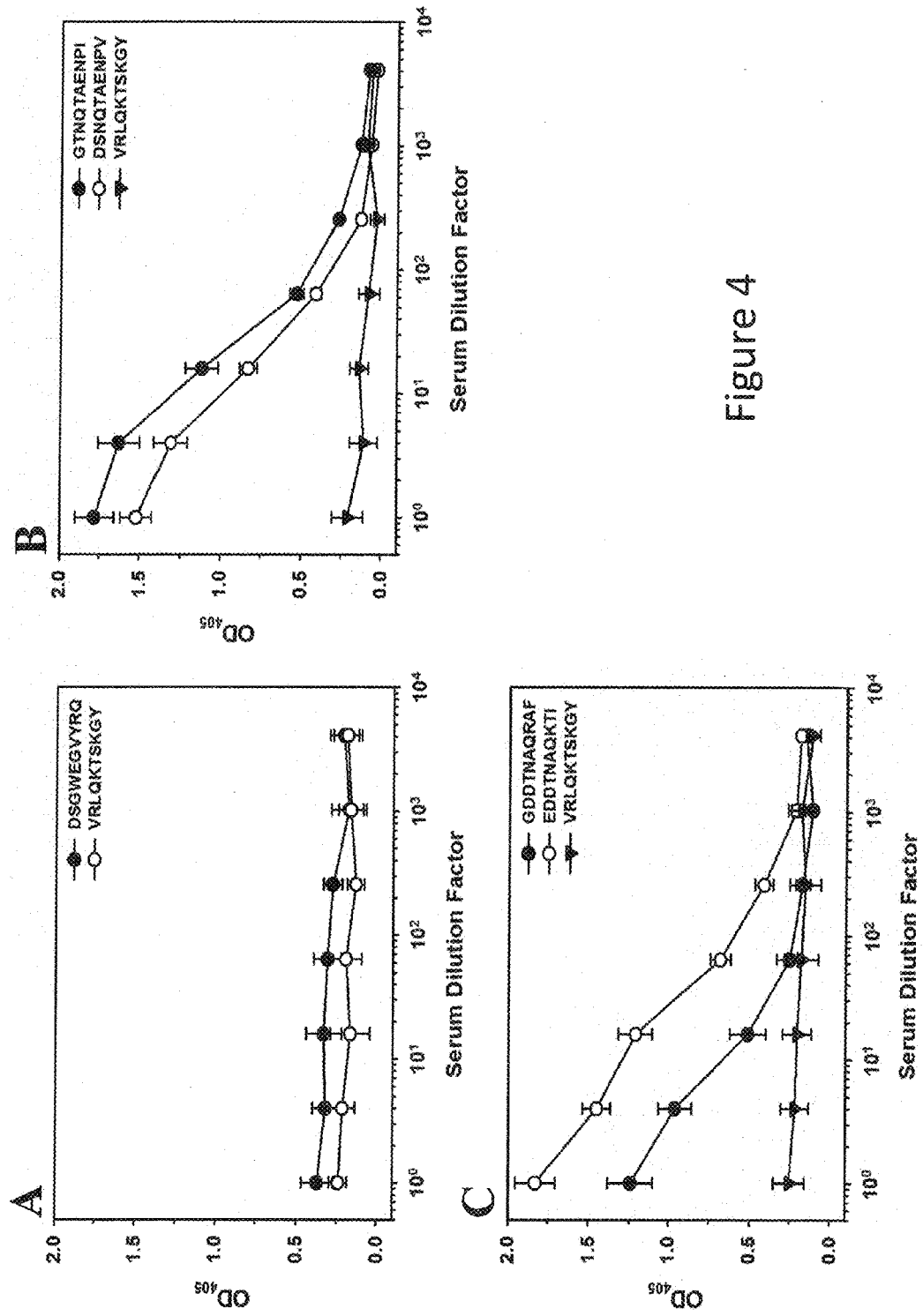
FIG. 4. ELISA showing binding of antisera raised against VLPs displaying 90 copies of affinity-selected peptides [DSGWEGVYRQ (SEQ ID NO: 6) for (A), GTNQTAENPI (SEQ ID NO: 19) for (B), and GDDTNAQRAF (SEQ ID NO: 32) for (C)], 90 copies of wild-type peptides [DSNQTAENPV (SEQ ID NO: 39) for (B) and EDDTNAQKTI (SEQ ID NO: 40) for (C)], or 90 copies of an irrelevant peptide [VRLQKTSKGY (SEQ ID NO: 41) for (A)-(C)] to corresponding affinity-selected peptides [DSGWEGVYRQ (SEQ ID NO: 6) for (A), GTNQTAENPI (SEQ ID NO: 19) for (B), and GDDTNAQRAF (SEQ ID NO: 32) for (C)]. Peptides were adsorbed to Immulon 2 HB 96-well plates for 2 hours at 37° C. and overnight at 4° C. and then incubated with diluted sera for 1 hour at 37° C. Plates were washed extensively with 1×PBS and then incubated with a horseradish peroxidase (HRP)-conjugated goat polyclonal antibody against mouse IgG for 1 hour at 37° C. Plates were then washed three times with 1×PBS, incubated with 2,2-Azinobis [3-ethylbenzothiazoline-6-sulfonic acid]-diammonium salt (ABTS) for 20 minutes at room temperature, and read at 405-nm. Error bars represent the mean+/−the standard deviation for n=2–3.

FIG. 4 ELISA showing binding of antisera raised against VLPs displaying 90 copies of affinity-selected peptides [DSGWEGVYRQ (SEQ ID NO: 6) for (A), GTNQTAENPI (SEQ ID NO: 19) for (B), and GDDTNAQRAF (SEQ ID NO: 32) for (C)], 90 copies of wild-type peptides [DSNQTAENPV (SEQ ID NO: 39) for (B) and EDDTNAQKTI (SEQ ID NO: 40) for (C)], or 90 copies of an irrelevant peptide [VRLQKTSKGY (SEQ ID NO: 40) for (A)-(C)] to corresponding affinity-selected peptides [DSGWEGVYRQ (SEQ ID NO: 6) for (A), GTNQTAENPI (SEQ ID NO: 19) for (B), and GDDTNAQRAF (SEQ ID NO: 32) for (C)]. Peptides were adsorbed to Immulon 2 HB 96-well plates for 2 hours at 37° C. and overnight at 4° C. and then incubated with diluted sera for 1 hour at 37° C. Plates were washed extensively with 1×PBS and then incubated with a horseradish peroxidase (HRP)-conjugated goat polyclonal antibody against mouse IgG for 1 hour at 37° C. Plates were then washed three times with 1×PBS, incubated with 2,2'-Azinobis [3-ethylbenzothiazoline-6-sulfonic acid]-diammonium salt (ABTS) for 20 minutes at room temperature, and read at 405-nm. Error bars represent the mean+/−the standard deviation for n=2-3.

Figure 5:
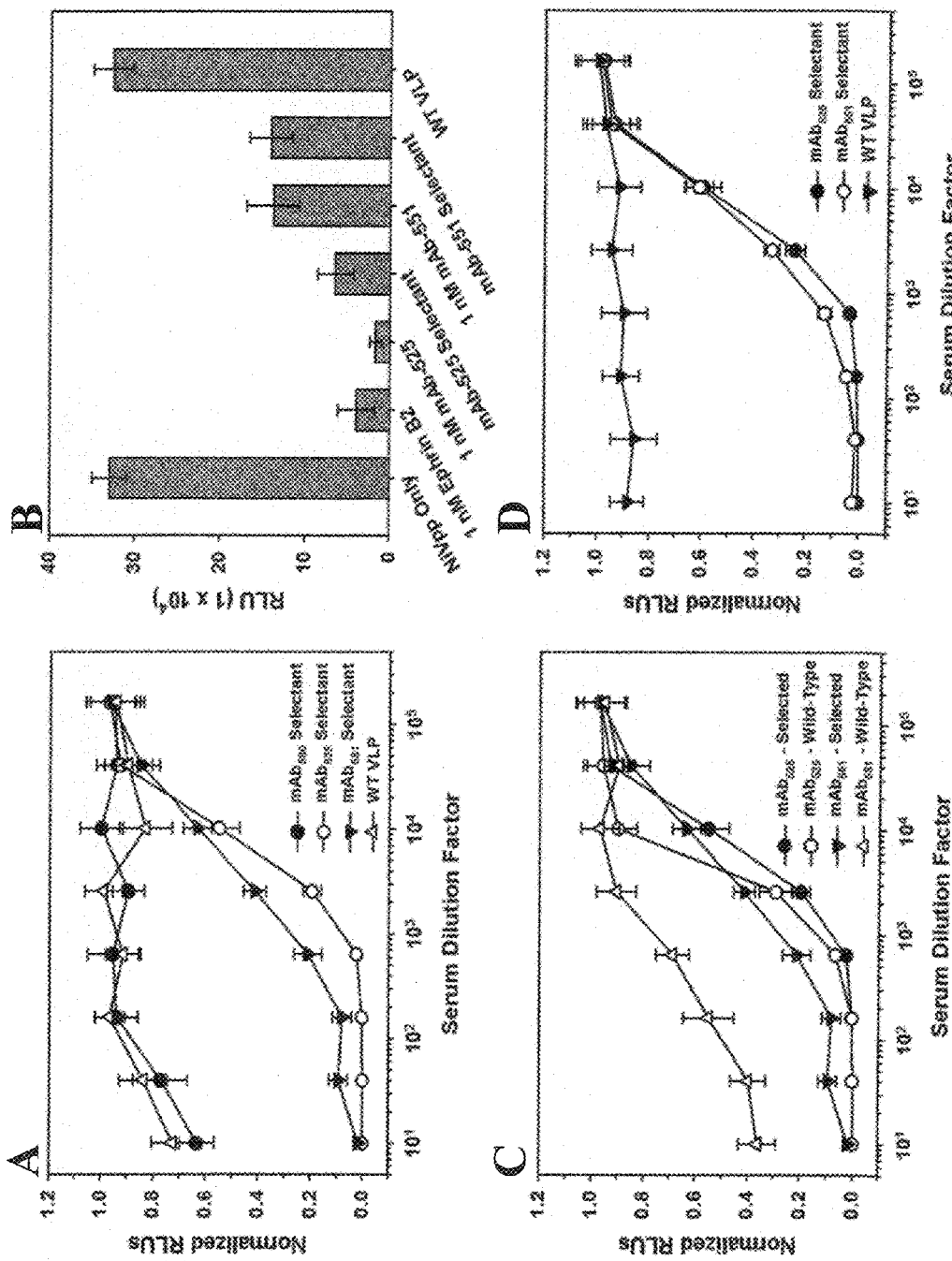
FIG. 5. Antisera raised against $mAb_{525}$ and $mAb_{551}$ selectants effectively neutralize NiVpp and HeVpp in vitro. (A) In vitro neutralization of a NiV pseudovirus (NiVpp) encoding Renilla luciferase by antiserum raised against the $mAb_{500}$ selectant, the $mAb_{525}$ selectant, the $mAb_{551}$ selectant, or wild-type VLPs ('WT VLP'). Antisera was diluted according to the x-axis, incubated with NiVpp for 30 minutes at room temperature, and applied to Vero cells; Renilla luciferase was developed 18 hours post-infection, and relative light units (RLUs) were measured using a luminometer and normalized based on the RLUs of Vero cells incubated with NiVpp in the absence of antiserum. (B) In vitro neutralization of NiVpp by 1 nM of ephrin B2, 1 nM of $mAb_{525}$, 1 nM of $mAb_{551}$, a 1:2560 dilution of antiserum raised against the $mAb_{525}$ selectant, a 1:2560 dilution of antiserum raised against the $mAb_{551}$ selectant, or a 1:2560 dilution of antiserum raised against wild-type VLPs. (C) In vitro neutralization of NiVpp by antiserum raised against VLPs displaying 90 copies of GTNQTAENPI (SEQ ID NO: 19) ('$mAb_{525}$—Selected'), DSNQTAENPV (SEQ ID NO: 39) ('$mAb_{525}$—Wild-Type'), GDDTNAQRAF (SEQ ID NO: 32) ('$mAb_{551}$—Selected'), or EDDTNAQKTI (SEQ ID NO: 40) ('$mAb_{551}$—Wild-Type'). (D) In vitro neutralization of a HeV pseudovirus (HeVpp) encoding Renilla luciferase by antiserum raised against the $mAb_{525}$ selectant, the $mAb_{551}$ selectant, or wild-type VLPs ('WT VLP'). All neutralization studies were conducted as described for (A). Error bars represent the mean+/−the standard deviation for n=3.

FIG. 5 shows an experiment that measures the ability of the antisera elicited in mice by the indicated VLP selectants to inhibit infection by a NiV-G-VSV and HeV-G-VSV pseudotypes. Infection results in expression of luciferase, the level of which is then measured as Relative Luminescence Units (RLU).

Figure 6:
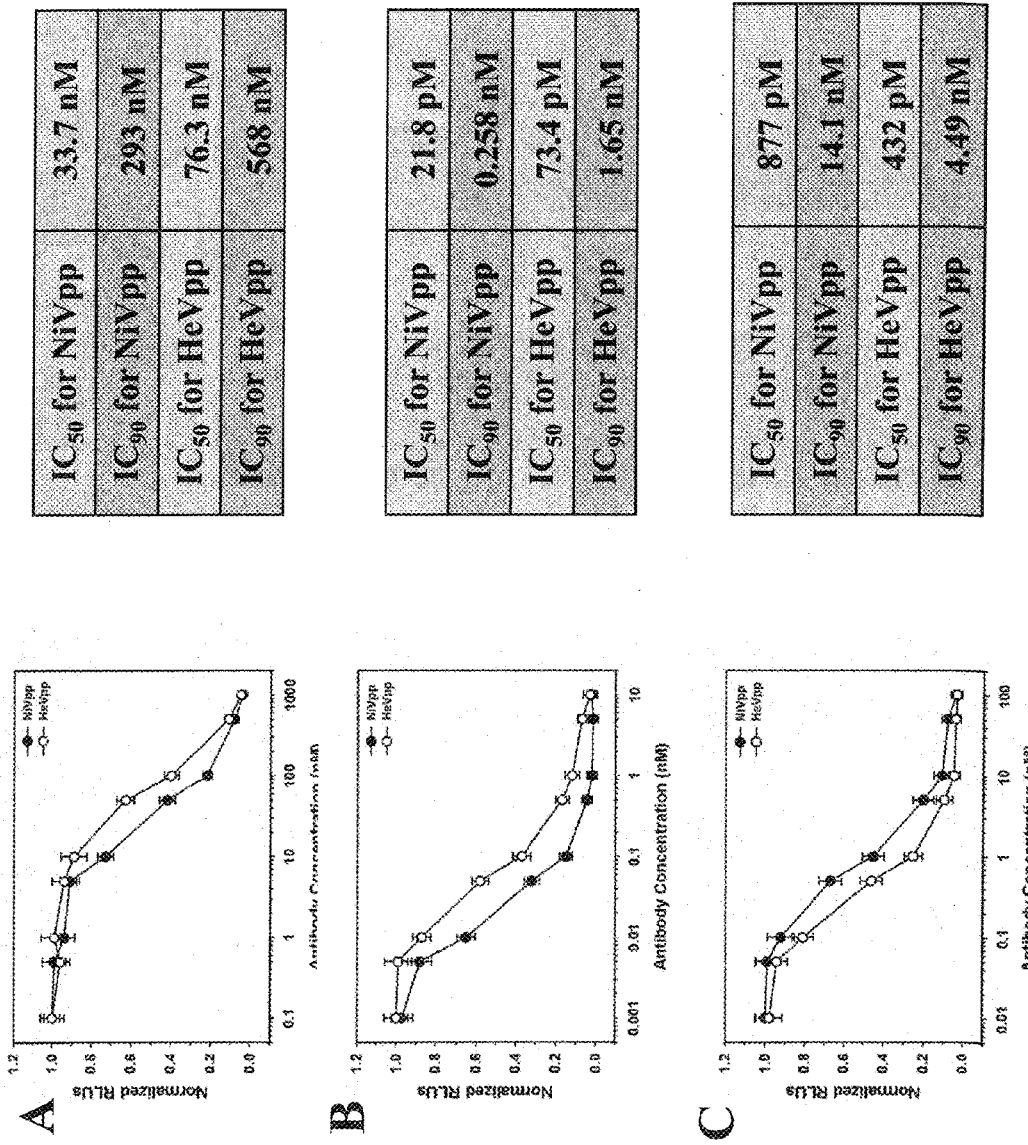
FIG. 6. In vitro neutralization of NiVpp and HeVpp encoding Renilla luciferase by $mAb_{500}$. The mAb concentrations denoted by the x-axis were incubated with NiVpp or HeVpp for 30 minutes at room temperature and applied to Vero cells; Renilla luciferase was developed 18 hours post-infection, and relative light units (RLUs) were measured using a luminometer and normalized based on the RLUs of Vero cells incubated with NiVpp or HeVpp alone. Error bars represent the mean+/−the standard deviation for n=3. (B) The concentrations of $mAb_{500}$ necessary to inhibit 50% ($IC_{50}$) or 90% ($IC_{w}$) of NiVpp or HeVpp infection in vitro. Panels A, B and C respectively show the neutralization activities of $mAb_{500}$, $mAb_{525}$, and $mAb_{551}$.

FIG. 6 shows the ability of the three monoclonal antibodies used in the affinity selections to neutralize the NiV-G-VSV and HeV-G-VSV pseudotypes.

Conclusions

Based on the above data, we conclude that affinity selection on three different Nipah-neutralizing monoclonal antibodies found VLPs displaying a variety of peptide sequences that match to varying degrees peptide sequences within the NiV glycoprotein. The resulting VLPs can elicit antibody responses in mice that recognize the G-protein in vitro and neutralize a NiV-G-VSV and HeV-G-VSV pseudotyped viruses. It may be noted that in at least one case (see FIG. 5C) the selected peptide is actually more effective than the corresponding wild-type NiV peptide at eliciting a neutralizing response. This illustrates one of the advantages of an affinity selection system that optimizes a peptide's sequence for interaction with the antibody, and thus improves the ability of a VLP displaying that sequence to elicit an antibody response whose activity mimics that of the selecting antibody. Not only does the affinity selection process allow for efficient mapping of epitopes within the amino acid sequence of the relevant antigen, but also may produce an improved version of that epitope.

REFERENCES

1. Caldeira J D, Medford A, Kines R C, Lino C A, Schiller J T, Chackerian B, Peabody D S: Immunogenic display of diverse peptides, including a broadly cross-type neutralizing human papillomavirus L2 epitope, on virus-like particles of the RNA bacteriophage PP7. *Vaccine* 2010, 28:4384-4393.
2. Chackerian B, Caldeira Jdo C, Peabody J, Peabody D S: Peptide Epitope Identification by Affinity Selection on Bacteriophage MS2 Virus-Like Particles. *J Mol Biol* 2011, 409:225-237.
3. Peabody D S: Subunit fusion confers tolerance to peptide insertions in a virus coat protein. *Arch Biochem Biophys* 1997, 347:85-92.
4. Peabody D S, Manifold-Wheeler B, Medford A, Jordan S K, do Carmo Caldeira J, Chackerian B: Immunogenic display of diverse peptides on virus-like particles of RNA phage MS2. *J Mol Biol* 2008, 380:252-263.

SEQUENCE LISTINGS

From FIG. 2, the following sequences are identified from the drawings:

<SEQ ID NO 1; PRT> PEVCWEGVYNDA
<SEQ ID NO 2; PRT> DIGWEGVYQA
<SEQ ID NO 3; PRT> LGWEAVYREA
<SEQ ID NO 4; PRT> GWDGVYQDSP
<SEQ ID NO 5; PRT> IGWDASYNEA
<SEQ ID NO 6; PRT> DSGWEGVYRQ
<SEQ ID NO 7; PRT> DLAWEGIYGK
<SEQ ID NO 8; PRT> DTGWDGVYQA
<SEQ ID NO 9; PRT> IGWEAVYKET
<SEQ ID NO 10; PRT> LAWDATYQEA
<SEQ ID NO 11; PRT> DVGWDGIFAE
<SEQ ID NO 12; PRT> ISFEGIYRQG
<SEQ ID NO 13; PRT> ADVAWDGIFA
<SEQ ID NO 14; PRT> TSWDAVYREH
<SEQ ID NO 15; PRT> SDVGWEASFA
<SEQ ID NO 16; PRT> DLSFEAAYQK
<SEQ ID NO 17; PRT> GWEASFARES
<SEQ ID NO 18; PRT> FLDSNQTAENPVFTV
<SEQ ID NO 19; PRT> GTNQTAENPI
<SEQ ID NO 20; PRT> GANQTAENPL
<SEQ ID NO 21; PRT> EANQTADNPI
<SEQ ID NO 22; PRT> EGNQTGENPL
<SEQ ID NO 23; PRT> GTNQTGENPA
<SEQ ID NO 24; PRT> TQQTGENPLG
<SEQ ID NO 25; PRT> TNQSGENPAS
<SEQ ID NO 26; PRT> ANQSADQPGK
<SEQ ID NO 27; PRT> GANNSADNPI
<SEQ ID NO 28; PRT> AANRTGENPG
<SEQ ID NO 29; PRT> LAEDDTNAQKTI
<SEQ ID NO 30; PRT> SATDDTNAQR
<SEQ ID NO 31; PRT> AADDTQAQKA
<SEQ ID NO 32; PRT> GDDTNAQRAF
<SEQ ID NO 33; PRT> TEDTNAQQGH
<SEQ ID NO 34; PRT> ADDTNSQRGY
<SEQ ID NO 35; PRT> GDESNSQNGI
<SEQ ID NO 36; PRT> GDETNGQGGW
<SEQ ID NO 37; PRT> PGEESNAQRA
<SEQ ID NO 38; PRT> AEDSNGRRSL

From page 5, in the description for FIG. 4, the following additional sequences are identified from the specification:

<SEQ ID NO 39; PRT> DSNQTAENPV
<SEQ ID NO 40; PRT> EDDTNAQKTI
<SEQ ID NO 41; PRT> VRLQKTSKGY

From page 21, the following additional sequences are identified from the specification:

<SEQ ID NO 42; PRT> EVCWEGVYND
<SEQ ID NO 43; PRT> SEDTNAQKTI
<SEQ ID NO 44; PRT> MPAENKKVRFENTTSDKG-KNPSKVIKSYYG TMDIKKINEGLLDSKILSAFNT-VIALLGSIVII VMNIMIIQNYTRSTDNQA-VIKDALQGIQQQI KGLADKIGTEIGPKVSLIDTSSTITIPANIGLLG SKISQSTASINENVNEKCKFTLPPLKIHECNIS CPN-PLPFREYRPQTEGVSNLVGLPDNICLQK TSNQILK-PKLISYTLPVVGQSGTCITDPLLAM DEGYFAY-SHLERIGSCSRGVSKQRIIGVGEVL DRGDEVPSLFMTNVWTPPNPNTVYHCSAVY NNE-FYYVLCAVSTVGDPILNSTYWSGSLMM TRLAVK-PKSNGGGYNQHQLALRSIEKGRYD KVMPYGPS-GIKQGDTLYFPAVGFLVRTEFKY NDSNCPITKCQYSKPENCRLSMGIRPNSHYIL RSGLLKYNLSDGENPKIVFIEISDQRLSIGSPS KVYDSLGQPVFYQASFSWDTMIKFGDVQTV NPLVVNWRDNTVISRPGQSQCPRFNTCPEIC WEGVYNDAFLIDRINWISAGVFLDSNQTAE NPVFTVFKDNEILYRAQLASEDTNAQKTITN CFLLKNKIWCISLVEIYDTGDNVIRPKLFAVK IPEQCT

---

What is claimed is:

1. A population of virus-like particles (VLPs) produced by a method comprising:
   (a) providing a population of VLPs that have been expressed by a prokaryote, wherein each of said VLPs comprises a coat polypeptide of a MS2 or PP7 bacteriophage, wherein said coat polypeptide is modified by insertion of an immunogenic heterologous peptide of Nipah Virus within the amino acid sequence of said coat polypeptide at a site corresponding to the A-B loop, wherein said heterologous peptide is displayed on said VLPs and said VLPs optionally encapsidate said bacteriophage mRNA; and
   (b) wherein said heterologous peptide comprises at least one peptide selected from the group consisting of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, and SEQ ID NO: 38; and
   (c) exposing said population of VLPs obtained in step (a) to Nipah Virus-neutralizing antibodies to bind to said VLPs, wherein said bound VLPs are isolated.

2. A population of VLPs according to claim 1 produced by repeating said method from 2 to 4 times.

3. A virus-like particle comprising a coat polypeptide of a MS2 or PP7 bacteriophage wherein said coat polypeptide is modified by insertion of an immunogenic heterologous peptide of Nipah Virus within the amino acid sequence of said coat polypeptide at a site corresponding to the A-B loop, wherein said heterologous peptide is displayed on said VLP and said VLP optionally encapsidates said bacteriophage mRNA, and said coat polypeptide of said bacteriophage is a single chain dimer comprising an upstream and downstream subunit, and wherein said heterologous peptide is selected from the group consisting of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37 or SEQ ID NO: 38.

4. The VLP according to claim 3, wherein said bacteriophage is PP7.

5. The VLP according to claim 3, wherein said bacteriophage is MS2.

6. The VLP according to claim 3, wherein said heterologous peptide is selected from the group consisting of: SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, or SEQ ID NO: 13.

7. The VLP according to claim 3, wherein said heterologous peptide is selected from the group consisting of: SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, or SEQ ID NO: 27.

8. The VLP according to claim 3, wherein said heterologous peptide is selected from the group consisting of: SEQ ID NO: 2, SEQ ID NO: 3, SEQ ID NO: 4 or SEQ ID NO: 5.

9. The VLP according to claim 3, wherein said heterologous peptide is selected from the group consisting of: SEQ ID NO: 28, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37 or SEQ ID NO: 38.

10. The VLP according to claim 3, wherein said heterologous peptide is selected from the group consisting of: SEQ ID NO: 2, SEQ ID NO: 3, SEQ ID NO: 4, SEQ ID NO: 5, SEQ ID NO: 19, SEQ ID NO: 20, SEQ ID NO: 21, SEQ ID NO: 22, SEQ ID NO: 30, SEQ ID NO: 31, SEQ ID NO: 32 or SEQ ID NO: 33.

11. The VLP according to claim 3, wherein said heterologous peptide is selected from the group consisting of: SEQ ID NO: 2, SEQ ID NO: 3, SEQ ID NO: 4, SEQ ID NO: 5 or SEQ ID NO: 6.

12. The VLP according to claim 3, wherein said heterologous peptide is selected from the group consisting of: SEQ ID NO: 19, SEQ ID NO: 20, SEQ ID NO: 21, SEQ ID NO: 22 or SEQ ID NO: 23.

13. The VLP according to claim 3, wherein said heterologous peptide is peptide is selected from the group consisting of: SEQ ID NO: 30, SEQ ID NO: 31, SEQ ID NO: 32, SEQ ID NO: 33 or SEQ ID NO: 34.

14. The VLP according to claim 3, wherein said heterologous peptide is SEQ ID NO: 19.

15. A virus-like particle according to claim 3 expressed by a prokaryote.

16. An immunogenic composition comprising a virus-like particle of claim 3.

17. A diagnostic assay or kit comprising a virus-like particle of claim 3.

18. A vaccine composition comprising an immunogenic composition according to claim 16.

* * * * *

SEQUENCE LISTING

```
<160> NUMBER OF SEQ ID NOS: 45

<210> SEQ ID NO 1
<211> LENGTH: 12
<212> TYPE: PRT
<213> ORGANISM: Artificial
<220> FEATURE:
<223> OTHER INFORMATION: NiV G-protein

<400> SEQUENCE: 1

Pro Glu Val Cys Trp Glu Gly Val Tyr Asn Asp Ala
1               5                   10

<210> SEQ ID NO 2
<211> LENGTH: 10
<212> TYPE: PRT
<213> ORGANISM: Artificial
<220> FEATURE:
<223> OTHER INFORMATION: NiV G-protein

<400> SEQUENCE: 2

Asp Ile Gly Trp Glu Gly Val Tyr Gln Ala
1               5                   10

<210> SEQ ID NO 3
<211> LENGTH: 10
<212> TYPE: PRT
<213> ORGANISM: Artificial
<220> FEATURE:
<223> OTHER INFORMATION: NiV G-protein

<400> SEQUENCE: 3

Leu Gly Trp Glu Ala Val Tyr Arg Glu Ala
1               5                   10

<210> SEQ ID NO 4
<211> LENGTH: 10
<212> TYPE: PRT
<213> ORGANISM: Artificial
<220> FEATURE:
<223> OTHER INFORMATION: NiV G-protein

<400> SEQUENCE: 4

Gly Trp Asp Gly Val Tyr Gln Asp Ser Pro
1               5                   10

<210> SEQ ID NO 5
<211> LENGTH: 10
<212> TYPE: PRT
<213> ORGANISM: Artificial
```

```
<220> FEATURE:
<223> OTHER INFORMATION: NiV G-protein

<400> SEQUENCE: 5

Ile Gly Trp Asp Ala Ser Tyr Asn Glu Ala
1               5                   10

<210> SEQ ID NO 6
<211> LENGTH: 10
<212> TYPE: PRT
<213> ORGANISM: Artificial
<220> FEATURE:
<223> OTHER INFORMATION: NiV G-protein

<400> SEQUENCE: 6

Asp Ser Gly Tyr Glu Gly Val Tyr Arg Gln
1               5                   10

<210> SEQ ID NO 7
<211> LENGTH: 10
<212> TYPE: PRT
<213> ORGANISM: Artificial
<220> FEATURE:
<223> OTHER INFORMATION: NiV G-protein

<400> SEQUENCE: 7

Asp Leu Ala Trp Glu Gly Ile Tyr Gly Lys
1               5                   10

<210> SEQ ID NO 8
<211> LENGTH: 10
<212> TYPE: PRT
<213> ORGANISM: Artificial
<220> FEATURE:
<223> OTHER INFORMATION: NiV G-protein

<400> SEQUENCE: 8

Asp Thr Gly Trp Asp Gly Val Tyr Gln Ala
1               5                   10

<210> SEQ ID NO 9
<211> LENGTH: 10
<212> TYPE: PRT
<213> ORGANISM: Artificial
<220> FEATURE:
<223> OTHER INFORMATION: NiV G-protein

<400> SEQUENCE: 9

Ile Gly Trp Glu Ala Val Tyr Lys Glu Thr
1               5                   10

<210> SEQ ID NO 10
<211> LENGTH: 10
<212> TYPE: PRT
<213> ORGANISM: Artificial
<220> FEATURE:
<223> OTHER INFORMATION: NiV G-protein

<400> SEQUENCE: 10

Leu Ala Trp Asp Ala Thr Tyr Gln Glu Ala
1               5                   10

<210> SEQ ID NO 11
<211> LENGTH: 10
<212> TYPE: PRT
<213> ORGANISM: Artificial
<220> FEATURE:
```

<223> OTHER INFORMATION: NiV G-protein

<400> SEQUENCE: 11

Asp Val Gly Trp Asp Gly Ile Phe Ala Glu
1               5                   10

<210> SEQ ID NO 12
<211> LENGTH: 10
<212> TYPE: PRT
<213> ORGANISM: Artificial
<220> FEATURE:
<223> OTHER INFORMATION: NiV G-protein

<400> SEQUENCE: 12

Ile Ser Phe Glu Gly Ile Tyr Arg Gln Gly
1               5                   10

<210> SEQ ID NO 13
<211> LENGTH: 10
<212> TYPE: PRT
<213> ORGANISM: Artificial
<220> FEATURE:
<223> OTHER INFORMATION: NiV G-protein

<400> SEQUENCE: 13

Ala Asp Val Ala Trp Asp Gly Ile Phe Ala
1               5                   10

<210> SEQ ID NO 14
<211> LENGTH: 10
<212> TYPE: PRT
<213> ORGANISM: Artificial
<220> FEATURE:
<223> OTHER INFORMATION: NiV G-protein

<400> SEQUENCE: 14

Thr Ser Trp Asp Ala Val Tyr Arg Glu His
1               5                   10

<210> SEQ ID NO 15
<211> LENGTH: 10
<212> TYPE: PRT
<213> ORGANISM: Artificial
<220> FEATURE:
<223> OTHER INFORMATION: NiV G-protein

<400> SEQUENCE: 15

Ser Asp Val Gly Trp Glu Ala Ser Phe Ala
1               5                   10

<210> SEQ ID NO 16
<211> LENGTH: 10
<212> TYPE: PRT
<213> ORGANISM: Artificial
<220> FEATURE:
<223> OTHER INFORMATION: NiV G-protein

<400> SEQUENCE: 16

Asp Leu Ser Phe Glu Ala Ala Tyr Gln Lys
1               5                   10

<210> SEQ ID NO 17
<211> LENGTH: 10
<212> TYPE: PRT
<213> ORGANISM: Artificial
<220> FEATURE:
<223> OTHER INFORMATION: NiV G-protein

```
<400> SEQUENCE: 17

Gly Trp Glu Ala Ser Phe Ala Arg Glu Ser
1               5                   10

<210> SEQ ID NO 18
<211> LENGTH: 15
<212> TYPE: PRT
<213> ORGANISM: Artificial
<220> FEATURE:
<223> OTHER INFORMATION: NiV G-protein

<400> SEQUENCE: 18

Phe Leu Asp Ser Asn Gln Thr Ala Glu Asn Pro Val Phe Thr Val
1               5                   10                  15

<210> SEQ ID NO 19
<211> LENGTH: 10
<212> TYPE: PRT
<213> ORGANISM: Artificial
<220> FEATURE:
<223> OTHER INFORMATION: NiV G-protein

<400> SEQUENCE: 19

Gly Thr Asn Gln Thr Ala Glu Asn Pro Ile
1               5                   10

<210> SEQ ID NO 20
<211> LENGTH: 10
<212> TYPE: PRT
<213> ORGANISM: Artificial
<220> FEATURE:
<223> OTHER INFORMATION: NiV G-protein

<400> SEQUENCE: 20

Gly Ala Asn Gln Thr Ala Glu Asn Pro Leu
1               5                   10

<210> SEQ ID NO 21
<211> LENGTH: 10
<212> TYPE: PRT
<213> ORGANISM: Artificial
<220> FEATURE:
<223> OTHER INFORMATION: NiV G-protein

<400> SEQUENCE: 21

Glu Ala Asn Gln Thr Ala Asp Asn Pro Ile
1               5                   10

<210> SEQ ID NO 22
<211> LENGTH: 10
<212> TYPE: PRT
<213> ORGANISM: Artificial
<220> FEATURE:
<223> OTHER INFORMATION: NiV G-protein

<400> SEQUENCE: 22

Glu Gly Asn Gln Thr Gly Glu Asn Pro Leu
1               5                   10

<210> SEQ ID NO 23
<211> LENGTH: 10
<212> TYPE: PRT
<213> ORGANISM: Artificial
<220> FEATURE:
<223> OTHER INFORMATION: NiV G-protein
```

```
<400> SEQUENCE: 23

Gly Thr Asn Gln Thr Gly Glu Asn Pro Ala
1               5                   10

<210> SEQ ID NO 24
<211> LENGTH: 10
<212> TYPE: PRT
<213> ORGANISM: Artificial
<220> FEATURE:
<223> OTHER INFORMATION: NiV G-protein

<400> SEQUENCE: 24

Thr Gln Gln Thr Gly Glu Asn Pro Leu Gly
1               5                   10

<210> SEQ ID NO 25
<211> LENGTH: 10
<212> TYPE: PRT
<213> ORGANISM: Artificial
<220> FEATURE:
<223> OTHER INFORMATION: NiV G-protein

<400> SEQUENCE: 25

Thr Asn Gln Ser Gly Glu Asn Pro Ala Ser
1               5                   10

<210> SEQ ID NO 26
<211> LENGTH: 10
<212> TYPE: PRT
<213> ORGANISM: Artificial
<220> FEATURE:
<223> OTHER INFORMATION: NiV G-protein

<400> SEQUENCE: 26

Ala Asn Gln Ser Ala Asp Gln Pro Gly Lys
1               5                   10

<210> SEQ ID NO 27
<211> LENGTH: 10
<212> TYPE: PRT
<213> ORGANISM: Artificial
<220> FEATURE:
<223> OTHER INFORMATION: NiV G-protein

<400> SEQUENCE: 27

Gly Ala Asn Asn Ser Ala Asp Asn Pro Ile
1               5                   10

<210> SEQ ID NO 28
<211> LENGTH: 10
<212> TYPE: PRT
<213> ORGANISM: Artificial
<220> FEATURE:
<223> OTHER INFORMATION: NiV G-protein

<400> SEQUENCE: 28

Ala Ala Asn Arg Thr Gly Glu Asn Pro Gly
1               5                   10

<210> SEQ ID NO 29
<211> LENGTH: 12
<212> TYPE: PRT
<213> ORGANISM: Artificial
<220> FEATURE:
<223> OTHER INFORMATION: NiV G-protein

<400> SEQUENCE: 29
```

Leu Ala Glu Asp Asp Thr Asn Ala Gln Lys Thr Ile
1               5                   10

<210> SEQ ID NO 30
<211> LENGTH: 10
<212> TYPE: PRT
<213> ORGANISM: Artificial
<220> FEATURE:
<223> OTHER INFORMATION: NiV G-protein

<400> SEQUENCE: 30

Ser Ala Thr Asp Asp Thr Asn Ala Gln Arg
1               5                   10

<210> SEQ ID NO 31
<211> LENGTH: 10
<212> TYPE: PRT
<213> ORGANISM: Artificial
<220> FEATURE:
<223> OTHER INFORMATION: NiV G-protein

<400> SEQUENCE: 31

Ala Ala Asp Asp Thr Gln Ala Gln Lys Ala
1               5                   10

<210> SEQ ID NO 32
<211> LENGTH: 10
<212> TYPE: PRT
<213> ORGANISM: Artificial
<220> FEATURE:
<223> OTHER INFORMATION: NiV G-protein

<400> SEQUENCE: 32

Gly Asp Asp Thr Asn Ala Gln Arg Ala Phe
1               5                   10

<210> SEQ ID NO 33
<211> LENGTH: 10
<212> TYPE: PRT
<213> ORGANISM: Artificial
<220> FEATURE:
<223> OTHER INFORMATION: NiV G-protein

<400> SEQUENCE: 33

Thr Glu Asp Thr Asn Ala Gln Gln Gly His
1               5                   10

<210> SEQ ID NO 34
<211> LENGTH: 10
<212> TYPE: PRT
<213> ORGANISM: Artificial
<220> FEATURE:
<223> OTHER INFORMATION: NiV G-protein

<400> SEQUENCE: 34

Ala Asp Asp Thr Asn Ser Gln Arg Gly Tyr
1               5                   10

<210> SEQ ID NO 35
<211> LENGTH: 10
<212> TYPE: PRT
<213> ORGANISM: Artificial
<220> FEATURE:
<223> OTHER INFORMATION: NiV G-protein

<400> SEQUENCE: 35

Gly Asp Glu Ser Asn Ser Gln Asn Gly Ile
1               5                   10

<210> SEQ ID NO 36
<211> LENGTH: 10
<212> TYPE: PRT
<213> ORGANISM: Artificial
<220> FEATURE:
<223> OTHER INFORMATION: NiV G-protein

<400> SEQUENCE: 36

Gly Asp Glu Thr Asn Gly Gln Gly Gly Trp
1               5                   10

<210> SEQ ID NO 37
<211> LENGTH: 10
<212> TYPE: PRT
<213> ORGANISM: Artificial
<220> FEATURE:
<223> OTHER INFORMATION: NiV G-protein

<400> SEQUENCE: 37

Pro Gly Glu Glu Ser Asn Ala Gln Arg Ala
1 5 10

<210> SEQ ID NO 38
<211> LENGTH: 10
<212> TYPE: PRT
<213> ORGANISM: Artificial
<220> FEATURE:
<223> OTHER INFORMATION: NiV G-protein

<400> SEQUENCE: 38

Ala Glu Asp Ser Asn Gly Arg Arg Ser Leu
1 5 10

<210> SEQ ID NO 39
<211> LENGTH: 10
<212> TYPE: PRT
<213> ORGANISM: Artificial
<220> FEATURE:
<223> OTHER INFORMATION: Wild-type peptide

<400> SEQUENCE: 39

Asp Ser Asn Gln Thr Ala Glu Asn Pro Val
1 5 10

<210> SEQ ID NO 40
<211> LENGTH: 10
<212> TYPE: PRT
<213> ORGANISM: Artificial
<220> FEATURE:
<223> OTHER INFORMATION: Wild-type peptide

<400> SEQUENCE: 40

Glu Asp Asp Thr Asn Ala Gln Lys Thr Ile
1 5 10

<210> SEQ ID NO 41
<211> LENGTH: 10
<212> TYPE: PRT
<213> ORGANISM: Artificial
<220> FEATURE:
<223> OTHER INFORMATION: Irrelevant peptide

<400> SEQUENCE: 41

Val Arg Leu Gln Lys Thr Ser Lys Gly Tyr

-continued

<210> SEQ ID NO 42
<211> LENGTH: 10
<212> TYPE: PRT
<213> ORGANISM: Artificial
<220> FEATURE:
<223> OTHER INFORMATION: NiV G-protein

<400> SEQUENCE: 42

Glu Val Cys Trp Glu Gly Val Tyr Asn Asp
1               5                   10

<210> SEQ ID NO 43
<211> LENGTH: 10
<212> TYPE: PRT
<213> ORGANISM: Artificial
<220> FEATURE:
<223> OTHER INFORMATION: NiV G-protein

<400> SEQUENCE: 43

Ser Glu Asp Thr Asn Ala Gln Lys Thr Ile
1               5                   10

<210> SEQ ID NO 44
<211> LENGTH: 633
<212> TYPE: PRT
<213> ORGANISM: Artificial
<220> FEATURE:
<223> OTHER INFORMATION: NiV G-protein

<400> SEQUENCE: 44

Met Pro Ala Glu Asn Lys Lys Val Arg Phe Glu Asn Thr Thr Ser Asp
1               5                   10                  15

Lys Gly Lys Asn Pro Ser Lys Val Ile Lys Ser Tyr Tyr Gly Thr Met
            20                  25                  30

Asp Ile Lys Lys Ile Asn Glu Gly Leu Leu Asp Ser Lys Ile Leu Ser
        35                  40                  45

Ala Phe Asn Thr Val Ile Ala Leu Leu Gly Ser Ile Val Ile Ile Val
    50                  55                  60

Met Asn Ile Met Ile Ile Gln Asn Tyr Thr Arg Ser Thr Asp Asn Gln
65                  70                  75                  80

Ala Val Ile Lys Asp Ala Leu Gln Gly Ile Gln Gln Gln Ile Lys Gly
                85                  90                  95

Leu Ala Asp Lys Ile Gly Thr Glu Ile Gly Pro Lys Val Ser Leu Ile
            100                 105                 110

Asp Thr Ser Ser Thr Ile Thr Ile Pro Ala Asn Ile Gly Leu Leu Gly
        115                 120                 125

Ser Lys Ile Ser Gln Ser Thr Ala Ser Ile Asn Glu Asn Val Asn Glu
    130                 135                 140

Lys Cys Lys Phe Thr Leu Pro Pro Leu Lys Ile His Glu Cys Asn Ile
145                 150                 155                 160

Ser Cys Pro Asn Pro Leu Pro Phe Arg Glu Tyr Arg Pro Gln Thr Glu
                165                 170                 175

Gly Val Ser Asn Leu Val Gly Leu Pro Asp Asn Ile Cys Leu Gln Lys
            180                 185                 190

Thr Ser Asn Gln Ile Leu Lys Pro Lys Leu Ile Ser Tyr Thr Leu Pro
        195                 200                 205

Val Val Gly Gln Ser Gly Thr Cys Ile Thr Asp Pro Leu Leu Ala Met
    210                 215                 220

-continued

```
Asp Glu Gly Tyr Phe Ala Tyr Ser His Leu Glu Arg Ile Gly Ser Cys
225                 230                 235                 240

Ser Arg Gly Val Ser Lys Gln Arg Ile Ile Gly Val Gly Glu Val Leu
            245                 250                 255

Asp Arg Gly Asp Glu Val Pro Ser Leu Phe Met Thr Asn Val Trp Thr
        260                 265                 270

Pro Pro Asn Pro Asn Thr Val Tyr His Cys Ser Ala Val Tyr Asn Asn
    275                 280                 285

Glu Phe Tyr Tyr Val Leu Cys Ala Val Ser Thr Val Gly Asp Pro Ile
290                 295                 300

Leu Asn Ser Thr Tyr Trp Ser Gly Ser Leu Met Met Thr Arg Leu Ala
305                 310                 315                 320

Val Lys Pro Lys Ser Asn Gly Gly Tyr Asn Gln His Gln Leu Ala
            325                 330                 335

Leu Arg Ser Ile Glu Lys Gly Arg Tyr Asp Lys Val Met Pro Tyr Gly
        340                 345                 350

Pro Ser Gly Ile Lys Gln Gly Asp Thr Leu Tyr Phe Pro Ala Val Gly
    355                 360                 365

Phe Leu Val Arg Thr Glu Phe Lys Tyr Asn Asp Ser Asn Cys Pro Ile
370                 375                 380

Thr Lys Cys Gln Tyr Ser Lys Pro Glu Asn Cys Arg Leu Ser Met Gly
385                 390                 395                 400

Ile Arg Pro Asn Ser His Tyr Ile Leu Arg Ser Gly Leu Leu Lys Tyr
            405                 410                 415

Asn Leu Ser Asp Gly Glu Asn Pro Lys Ile Val Phe Ile Glu Ile Ser
        420                 425                 430

Asp Gln Arg Leu Ser Ile Gly Ser Pro Ser Lys Val Tyr Asp Ser Leu
    435                 440                 445

Gly Gln Pro Val Phe Tyr Gln Ala Ser Phe Ser Trp Asp Thr Met Ile
450                 455                 460

Lys Phe Gly Asp Val Gln Thr Val Asn Pro Leu Val Val Asn Trp Arg
465                 470                 475                 480

Asp Asn Thr Val Ile Ser Arg Pro Gly Gln Ser Gln Cys Pro Arg Phe
            485                 490                 495

Asn Thr Cys Pro Glu Ile Cys Asn Pro Leu Val Val Asn Trp Arg Asp
        500                 505                 510

Asn Thr Val Ile Ser Arg Pro Gly Gln Ser Gln Cys Pro Arg Phe Asn
    515                 520                 525

Thr Cys Pro Glu Ile Cys Trp Glu Gly Val Tyr Asn Asp Ala Phe Leu
530                 535                 540

Ile Asp Arg Ile Asn Trp Ile Ser Ala Gly Val Phe Leu Asp Ser Asn
545                 550                 555                 560

Gln Thr Ala Glu Asn Pro Val Phe Thr Val Phe Lys Asp Asn Glu Ile
            565                 570                 575

Leu Tyr Arg Ala Gln Leu Ala Ser Glu Asp Thr Asn Ala Gln Lys Thr
        580                 585                 590

Ile Thr Asn Cys Phe Leu Leu Lys Asn Lys Ile Trp Cys Ile Ser Leu
    595                 600                 605

Val Glu Ile Tyr Asp Thr Gly Asp Asn Val Ile Arg Pro Lys Leu Phe
610                 615                 620

Ala Val Lys Ile Pro Glu Gln Cys Thr
625                 630
```

```
<210> SEQ ID NO 45
<211> LENGTH: 12
<212> TYPE: PRT
<213> ORGANISM: Artificial
<220> FEATURE:
<223> OTHER INFORMATION: NiV G-protein

<400> SEQUENCE: 45

Leu Ala Ser Glu Asp Thr Asn Ala Gln Lys Thr Ile
1               5                   10
```